US005807102A

United States Patent [19]

Lang et al.

[11] Patent Number: 5,807,102

[45] Date of Patent: Sep. 15, 1998

[54] DEVICE FOR HOLDING A PREFERABLY PLATE-FORM IMPLEMENT, SERVING FOR FORMING TEETH, IN PARTICULAR A POSITIONING CALOTTE, IN AN ARTICULATOR

[75] Inventors: Hans Walter Lang, Leutkirch; Alfred Straka, Isny, both of Germany

[73] Assignee: Kaltenbach & Voigt GmbH & Co., Biberach, Germany

[21] Appl. No.: 299,578

[22] Filed: Sep. 1, 1994

[30] Foreign Application Priority Data

Sep. 7, 1993 [DE] Germany .......................... 43 30 296.3

[51] Int. Cl.[6] .................................................... A61C 11/00

[52] U.S. Cl. ................................. 433/64; 433/54; 433/66

[58] Field of Search ................................. 433/54, 57, 58, 433/59, 61, 62, 63, 64, 65, 66, 67

[56] References Cited

U.S. PATENT DOCUMENTS

| | | | |
|---|---|---|---|
| 2,930,127 | 3/1960 | Mann et al. | 433/61 |
| 3,636,634 | 1/1972 | De Pietro | 433/57 |
| 4,196,518 | 4/1980 | Benzaria | 433/60 |
| 4,260,377 | 4/1981 | Hobo et al. | 433/58 |
| 4,323,346 | 4/1982 | Ben | 433/58 |
| 4,659,311 | 4/1987 | Raskin | 433/55 |
| 4,758,155 | 7/1988 | Marino | 433/58 |
| 4,797,097 | 1/1989 | Cohn | 433/64 |
| 5,026,282 | 6/1991 | Koike | 433/62 |
| 5,334,017 | 8/1994 | Lang et al. | 433/57 |

FOREIGN PATENT DOCUMENTS

| | | |
|---|---|---|
| 42 11 004 | 10/1993 | Germany . |
| 42 11 016 | 10/1993 | Germany . |
| 42 11 018 | 10/1993 | Germany . |
| 42 11 020 | 10/1993 | Germany . |

*Primary Examiner*—Ren Yan

*Attorney, Agent, or Firm*—Scully, Scott, Murphy & Presser

[57] ABSTRACT

In a device (51) for holding an in particular plate-like implement (52) serving for forming teeth, in particular a positioning calotte, in an articulator (1), having a holder (55) for the implement (52) which is held on the articulator (1), upon employment of an articulator (1) with a detachable upper part (37) and upon employment of only the lower part (35) of the articulator (1) the holder (55) is mounted on the joint parts (36) of the lower part (35) pivotably about the pivot axis (5) containing the joint parts (36).

17 Claims, 2 Drawing Sheets

31
15
26,27
37
46a
46b
9,36
11,12
44
43
68
23b
3
5
7
39
38
50
40
46
42
43
13,19
22
1
26,27
21
7
6,35
23a
2

5
53
54
73
64
63
51
62
83
59
56
36a
57
58
48
84
65
76
52
55
61
7
13,19
2

73
75
62
71
54
72
63
53
87
85
83
86
r
84
56
81
76
57
82
58
52
52a
52b

69

52
53
83
76
84
58
61
77
56
64
66
78
85
65
57
67
68
69

DEVICE FOR HOLDING A PREFERABLY PLATE-FORM IMPLEMENT, SERVING FOR FORMING TEETH, IN PARTICULAR A POSITIONING CALOTTE, IN AN ARTICULATOR

BACKGROUND OF THE INVENTION

1. Field of the Invention

According to the classical teachings on articulation, for the stabilising of full dentures the artificial tooth rows have to be so positioned that during each individual biting phase as far as possible all teeth maintain contact and individual tooth sections, in particular in the rear region do not gape apart. The so-called occlusion curve (Spee's curve) is mentioned as such a contact provider.

When determining the depth of the curve it has to be taken into account that the lower teeth should stand perpendicularly to the progression of the alveolar ridge. As the progression of the ridge is usually concave in the side teeth region, the area around the first molar automatically presents itself as the deepest point of the curve.

The extent of the spherical curvature of the occlusion curve also depends on many other factors, such as incisor overlap, cuspidal height and condylar trajectory.

2. Discussion of the Prior Art

In the classical method of tooth positioning for full dentures firstly the lower front teeth are set up in accordance with the wax wall height which the dentist has determined on the patient. After setting up the front teeth the canine teeth are positioned. The molar teeth and premolar teeth are set up last. It is in particular important for these tooth groups that the occlusion curve is taken into account. For this purpose, it is known to use a so-called positioning calotte. For holding the positioning calotte above the teeth of the lower jaw it has already been suggested to hold the positioning calotte in the region of the upper jaw base plate on the upper articulator arm.

The previous holding of such an implement is disadvantageous for several reasons. A first disadvantage is that the upper part of the articulator impairs the view and manual access when working on the denture. Also, this mounting is problematic with regard to the desired orientation of the positioning calotte.

Known positioning calottes consist of metal sheet which, with regard to the calotte shape, is cupped.

SUMMARY OF THE INVENTION

The object of the invention is to so configure a device of the kind mentioned in the introduction that the tooth forming or an examination of the model or artificial teeth can be more readily carried out.

With the device according to the invention the upper part of the articulator is no longer needed. The outlay is thus reduced as the upper part is not necessary or can be employed for other purposes, in particular if it matches the lower part of a second articulator. Further, the view of the teeth and manual access are improved, which considerably facilitates the work to be done and promotes the quality of the prothesis or prothesis parts. The mounting, in accordance with the invention, of the holder on the joint parts of the lower part of the articulator makes possible an easy and readily handled mounting or dismounting on the lower part, whereby in the tilted up or tilted back condition of the holder it is possible to do work unhindered.

Within the scope of the invention it is possible to use either an articulator with a removable upper part or to use only the lower part of an articulator, which is for example used only for positioning the teeth.

The invention also relates to a positioning calotte which likewise improves the view of the teeth, can be manufactured simply, quickly and economically and also offers facilitation of the work to be done with regard to particular measures for the forming of the teeth.

Set forth herein below are features which contribute to problem solving, and make easier the positioning and fixing of the implement and lead to economically manufacturable and compact constructions.

BRIEF DESCRIPTION OF THE DRAWINGS

The invention and further advantages achievable thereby will be described in more detail below, with reference to preferred exemplary embodiments and to the drawings, which show.

DETAILED DESCRIPTION OF THE PREFERRED EMBODIMENT

Figure 1:
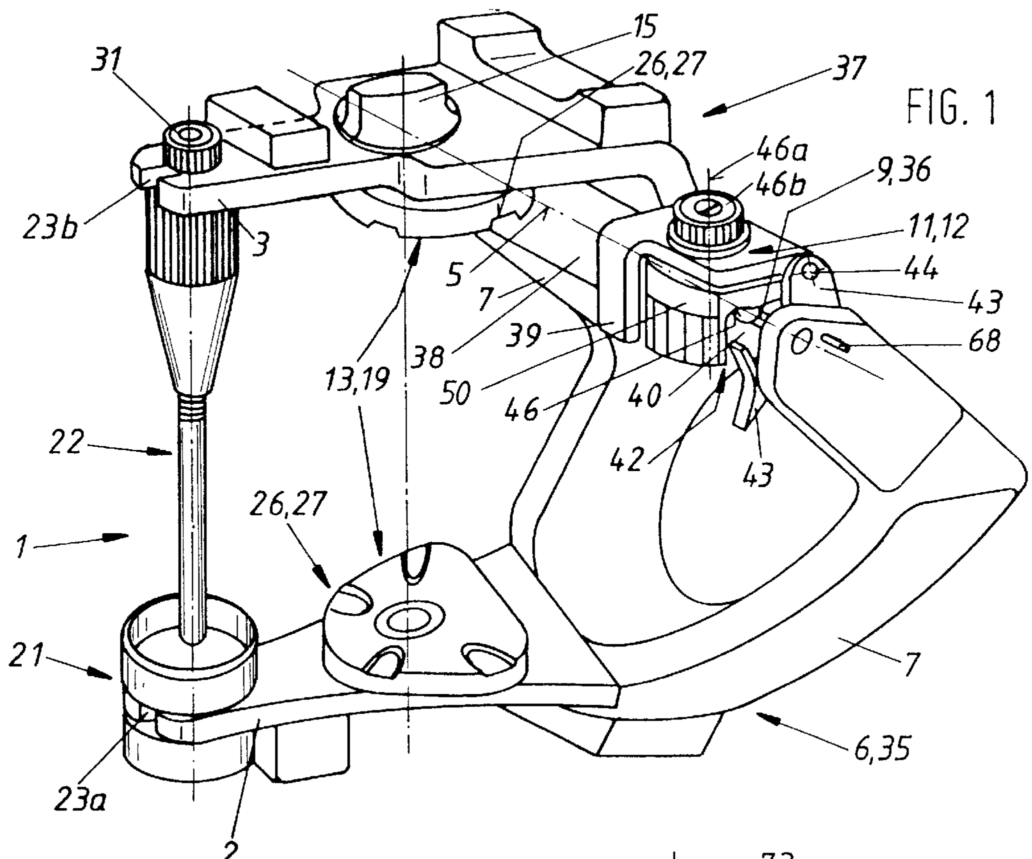
FIG. 1 an articulator which can be advantageously utilized within the scope of the invention, in a perspective view.
Figure 2:
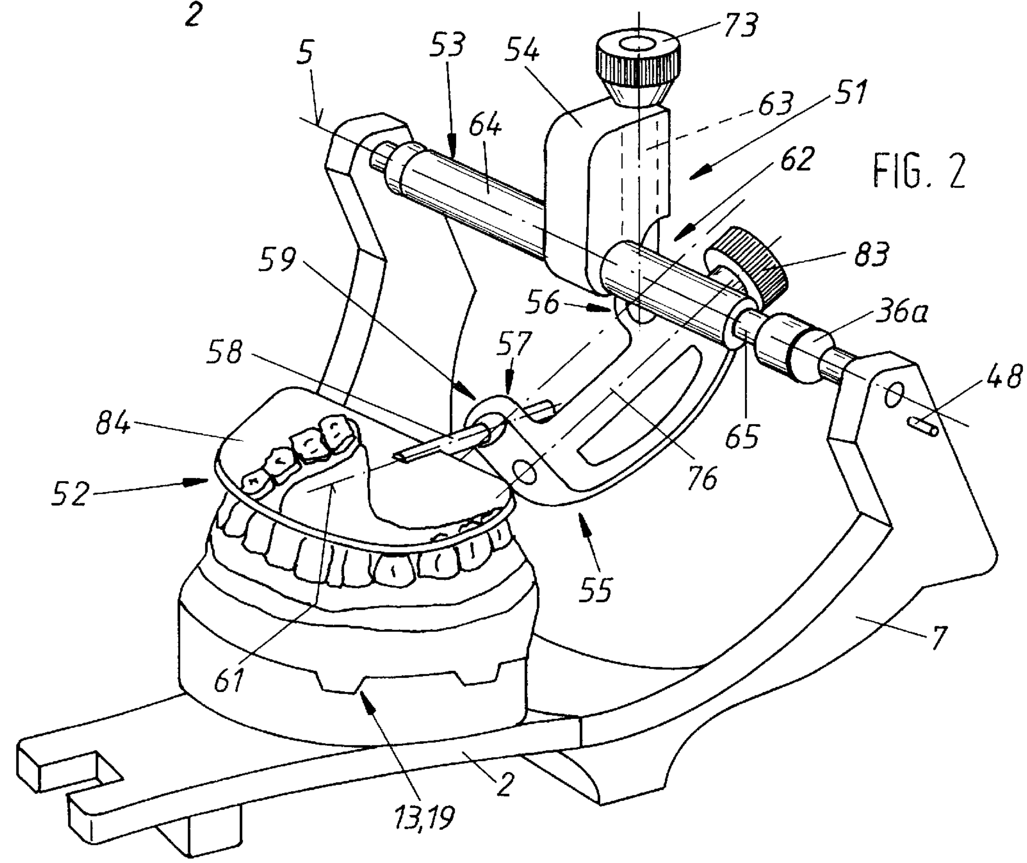
FIG. 2 the lower part of the articulator with a device according to the invention for holding a positioning calotte.
Figure 3:
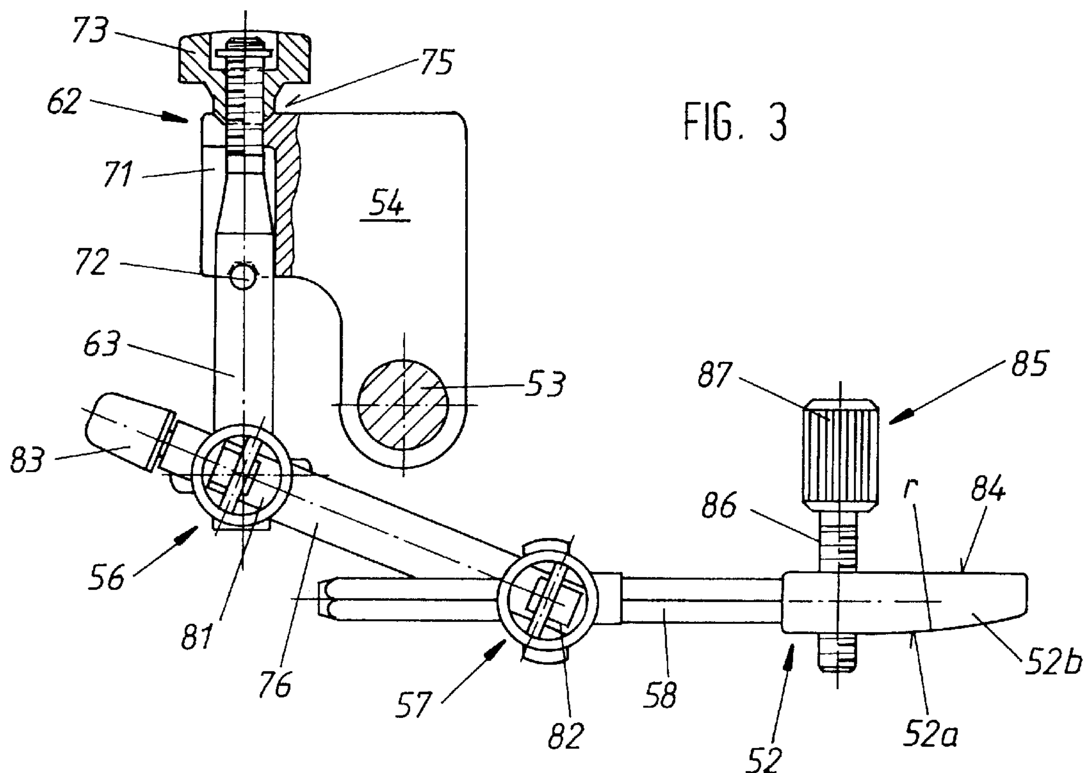
FIG. 3 the holder with a positioning calotte in a side view from the left.
Figure 4:
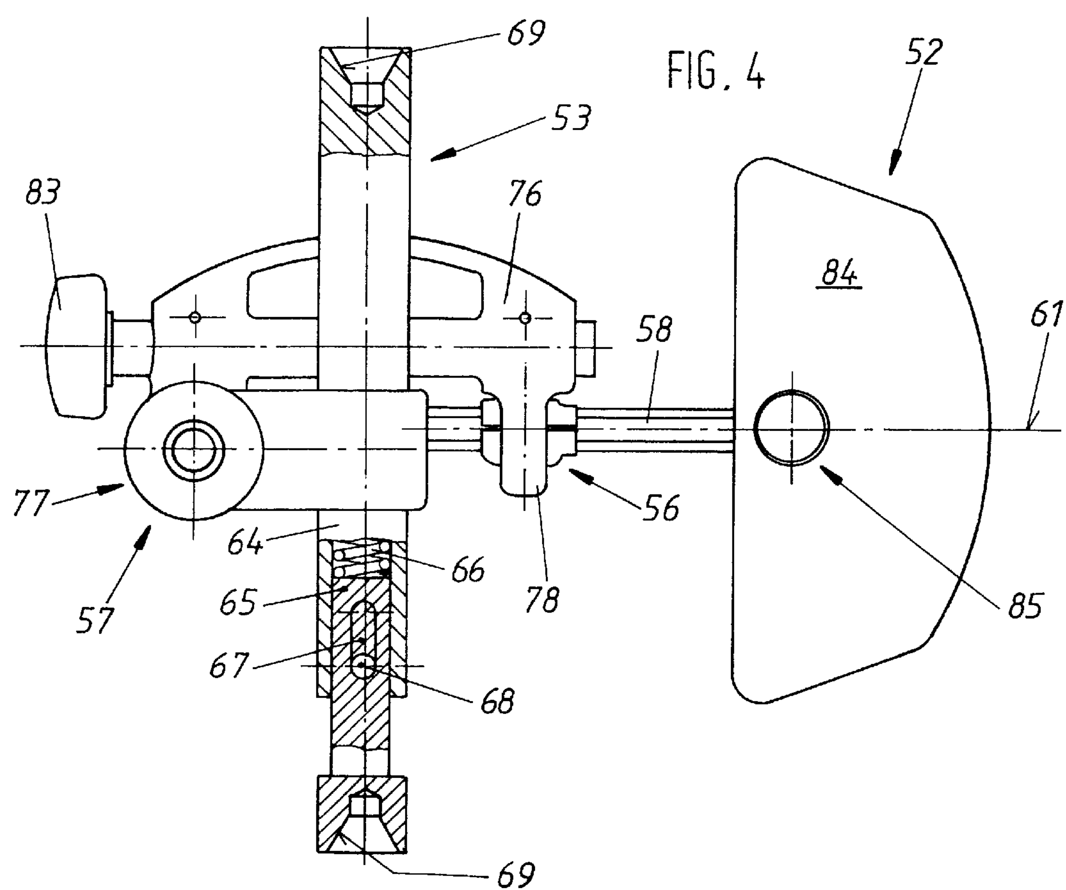
FIG. 4 the holder and the positioning calotte in a plan view.

The articulator has a lower articulator arm 2 and an upper articulator arm 3, of which the latter is mounted pivotally around pivot axis 5 extending from the front rearwardly and at right-angles to the vertical longitudinal middle plane E1 of the articulator pivotable on a U-shaped support or frame 6 having two lateral, upwardly extending, frame limbs 7. The pivot bearing parts 9 on the frame are arranged on the two ends of the frame limbs 7. Preferably, this is a so-called Arcon-articulator with rotary or swivel slide joints 11, of which the slide guide 12 is on the upper articulator arm 3. In the rear or middle region of the articulator arms 2, 3, on their sides facing towards each other, there are provided respective positioning locations 13 for associated tooth models or tooth model base parts, which are each positionable and fixable by means of a screw 15 penetrating through the articulator arm 2,3 in a through hole and by positioning pins projecting from the articulator arms 2, 3. In the Figures two primary bases 19 for a lower jaw model and an upper jaw model UK, OK are represented. On the forward end of the one articulator arm 2, 3, in the present case the lower articulator arm 2, an incisor table 21 is fixed, on which a telescopable supporting pin 22 extending in an upright direction is releasably supported at its free end, which pin is exactly positioned and fastened, releasably, on the end of the other articulator arm, in the present case the upper articulator arm 3. Preferably the fastening or receiving elements for the incisor table and the supporting pin 22 are the same or match each other, so that the incisor table and the supporting pin 22 are respectively fixable in mutually opposing positions either on the upper or on the lower articulator arm 2, 3. For mounting there serve respective mounting slots 23*a*, 23*b*, which preferably extend in the longitudinal middle plane, penetrate the associated articulator arm 2, 3 vertically, and open out at its free end. Into these like mounting slots, selectively either the incisor table 21 or a supporting pin 22 is mountable, with an appropriately matching waist formation, up to ends of the slots which correspond with one another and form the stops which limit the insertion movement, and can be screwed to the associated articulator 2, 3 by means of a screw part 31.

The articulator 1 consists of a lower part 35, comprising the lower articulator arm 2, the frame 6 and the joint heads 36 which project coaxially inwardly from the interior sides of the frame limbs 7, and an upper part 37, which comprises the upper articulator arm 3, a joint boss part 38 and two joint housings 39 attached to the sides of the boss part, in which housings the joint heads 36 are mounted in respective swivel slide joints 11. The upper part 37 is releasably held in the swivel slide joints 11 by means of the two center locks 42 associated with the joint housings 39. Each center lock 42 has a C-shaped lock shackle 43 which in its locking position, swung in around a transverse axis 44, engages below—preferably from the rear to the fore—the associated joint head 36 which extends horizontally inwardly, and herethrough fastens into the joint recess 40 present, which is open below and to the sides.

From the closing bite position, movements of the lower jaw can be simulated, which correspond to the anatomical reality of the human body. However, with the present embodiment, it is not the lower jaw or the lower part 35, but the upper part 37 together with the upper jaw which can be moved relative to the lower part 35 (Arcon-articulator).

The articulator 1 can be either a non-adjustable articulator, which is set in accordance with mean values, or an adjustable articulator, the joint guiding surfaces of which are preferably adjustable in several respects and can thus be adjusted to the anatomical reality of the head of the patient.

Below, four degrees of freedom are described for the swivel slide joints 11.

A first degree of freedom comprises a pivot bearing, in which the associated joint housing 39 is rotatable around the swivel axis 5 and is fixable in the respective rotational disposition achieved by means of a fixing device (not shown). Thus, an inclination of the sagittal guiding surface 46 is adjustable.

The second degree of freedom is formed by a pivot bearing, in which in each case a bearing part 50 having the sagittal guiding surface and the Bennett guiding surface is rotatable around a vertical pivot axis 46*a* and fixable in the respective pivot position achieved by means of a fixing element 46*b*. Thereby, a Bennett angle can be selectively set.

The third degree of freedom of one or both the bearing parts 39 consists in that it or they is or are adjustable in the longitudinal direction of the swivel axis 5 and is or are fixable in the respective adjustment position. This is made possible by means of a transversely directed lateral adjustment guide, which is (not shown) integrated into the associated joint housing 39.

A fourth degree of freedom consists in the adjustment of lateral guide parts, of differing radial dimensions (stepwise or curve form), rearwardly bounding the joint recess 40, by rotation or exchange, and to thereby realize different shift angles (not shown).

The device 51 for holding the positioning calotte consists of several main parts, namely a joint part, mountable on the ball heads 36*a* of the articulator lower part 35, in the form of a telescopic rod 53 with a connection part 54, and a holder 55 with two joints 56, 57, longitudinally positioned one after the other, for the positioning calotte 52, which has a carrier rod 58 projecting approximately horizontally forwardly beyond it, which is insertable into a plug-in socket 59 of the holder 55 and is therein rotatable around its longitudinal middle axis 61 and longitudinally displaceable and releasably fixable.

A second plug-in connection 62 is provided between the connection part 54 and a preferably upright support shaft 63 of the holder 55, which is accessible in particular from behind with regard to the connection part 54.

The telescopic rod 53 comprises an outer tube 64 and an inner part 65, which is inserted at one end into the outer tube and is biassed outwardly by a compression spring 66 arranged in the outer tube 64 and is secured against complete ejection from the outer tube 64 by means of a pin 68 penetrating the inner part in a longitudinal slit 67 and penetrating the outer tube 64. At the two opposite ends of the outer tube 64 and the inner part 65 there are respective conical centering recesses 69 provided, with which the telescopic rod 53 is mounted onto the respective ball heads 36*a* from the inside and pre-loaded, whereby a rotational bearing is ensured which allows for rotation around the swivel axis 5.

The connection part 54 is a block-like body projecting from the outer tube 64, preferably upwardly and rearwardly with an angled form, which body is mounted onto the outer tube 64 by means of a bore and is rigidly connected thereto. On one of its end faces, in this case on the rearward face, the connection part 54 has a vertical insertion slit 71 which is open to the rear, in which the support shaft 63 is insertable and fixable with little lateral play for movement. For this there serves a shoulder, preferably formed by a transverse pin 72, on the support shaft 63, which shoulder bears against the lower side of the connection part 54 and is tensionable against the connection part 54 by means of a hand nut 73, which is screwable onto the support shaft 63 projecting upwardly beyond the connection part 54. Preferably a centering is provided for the thus formed plug-in socket 62, which is in the present embodiment formed by a transverse groove, receiving the pin 72, on the lower side of the connection part 54 and a conical surface 75 on the lower end of the hand nut 73, whereby the latter is centered at the upper edge of the longitudinal slit 71, in particular at a conical edge diffraction.

Both the joints 56, 57 have, along with the longitudinal displaceability in the plug-in socket 59, so many degrees of freedom that the positioning calotte 52 is spatially positionable and adjustable. Preferably both the joints 56, 57 are ball joints. The joint 56 is arranged between the support shaft 63 and a preferably bow-shaped holder part 76, whereby the support shaft 63 can be fixedly connected with the corresponding joint ball. The second joint 57 is arranged between the holder part 76 and the carrying rod 58, whereby the associated joint ball has the associated hole in which the carrying rod 58 is seated. The joints 56, 57 are each arranged in a respective lateral attachment 77, 78 of the thus bow or U-shaped holder part 76 in which the joint balls 81, 82 are seated. Both joints 56, 57 are selectively fixable by means of a common hand-screw 83 which acts against the joint balls 81, 82 and thereby clamps these in their bearings by means of a right-handed and a left-handed screw thread and by means of clamping parts (not shown) displaceable through rotation of the hand-screw 83. The joint ball 82 receiving the carrying rod 58 is slit longitudinally so that by means of the hand-screw 83 the carrying rod 58 is also fixable in selectable positions with regard to its longitudinal displaceability and its rotation.

The holder 55 is described in earlier German patent application P 42 11 018.1-35, the articulator is described in German patent application P 42 11 020.3-35, the support pin 22 with the incisor table 21 is described in P 42 11 008.4-35, and an associated facial arc is described in P 42 11 016.5-35. In order to avoid repetition, reference is made to these descriptions and drawings to the fullest extent. The articulator 1 has positioning elements, in this case projecting spikes 48, on its outer sides on which elements the facial arc can be mounted with corresponding positioning elements, in this case centering recesses, arranged on its side arms.

The positioning calotte 52 is adapted, in its plan view, to the course or form of the row of teeth. Its underside 52*a* is convexly curved, in the sense of the occlusion curve, e.g. with a radius of curvature r of about 125 mm. Hereby, the positioning calotte is suitable for providing tooth cusp inclinations from about 25ϕ to 28ϕ. These are the most usually applicable tooth forms, such as Ivoclar, De Try, Lindauer teeth and the like. Calottes with other radii of curvature can be used as needed and as required.

The upper side of the positioning calotte 52 is a plane upper surface 84 which preferably extends parallel to the longitudinal middle axis of the carrying rod 58 and, in the installed position, preferably horizontally. The body of the positioning calotte is of plastics, preferably transparent plastics, and can thus be manufactured with precision, quickly and economically. The carrying rod 58 can be formed integrally or as a separate constructional component, in particular of metal, which is attached or embedded in the calotte body 52*b*. The transparency of the calotte body 52*b* improves not only the view from above of the row of teeth, but also enables markings, e.g. coloured lines, to be provided on the lower and/or upper side of the calotte body 52*b*, which for example facilitate the work to be done. Here, for example, the indication of the middle of the jaw ridge by means of colour lines or the like, on or below the calotte body 52*b*, may be involved. The calotte surface 52*a* and the upper surface 84 are preferably surfaces of the section of a sphere.

The central fissure of the false tooth, the statical middle point, can thus be positioned on the jaw ridge free of moment forces.

The positioning calotte 52 preferably has associated with it a grip piece 85, in particular arranged above the calotte, with which it can be manually grasped, displaced and held, for positioning thereof. In the present embodiment, a grip post 86 is preferably provided with a thickened head 87 which preferably projects upwardly from the calotte body 52*a*, in the region of its separation region and, for example, can be placed and fixed in a vertical hole of the calotte body 52*a*.

As is the facial arc, the articulator 1 is so conceived that the Camper's plane (CE) extends parallel to the horizontal table surface carrying the articulator 1. Given that this table surface is horizontal, the articulator arms 2, 3 in their working position, and the first guide 31 with the indicator 33 indicating the subnasal anterior point, extend horizontally. Consequently, the occlusion plane is also substantially horizontally arranged.

With its curved lower surface 52*a*, the calotte is associated with the retromolar tubercle, which is divided into thirds. The rearward alignment is the upper third, the already positioned UK (upper jaw) front teeth are to be seen as the forward alignment.

For this work, the articulator upper part 37 can be removed. This is of great importance, since for this work a good view of the UK (upper jaw) model is needed. With this conception, neither is a supporting pin 22 needed, which likewise facilitates access.

When the calotte has been aligned, the located disposition can be readily and exactly fixed with the aid of the middle screw 83.

In contrast to the usual calottes, this new development can also be employed when the full denture model is articulated together with the facial arc.

We claim:

1. A device (51) for holding a positioning calotte (52) for the forming of teeth in an articulator (1), said articulator including a lower articulator part (35) and an upper articulator part (37); a pair of swivel slide joints (11) being located at opposite ends of a vertical longitudinal center plane extending rearwardly from the front of said device, said swivel slide joints (11) connecting said upper articulator part (37) to said lower articulator part (35), each of said swivel slide joints (11) respectively having a slide guide (12) arranged on the upper articulator part (37) and a joint element (36) arranged on the lower articulator part (35) guided within an associated said slide guide (12); a holder (55) on said articulator for said positioning calotte (52) extending rearwardly from positioning calotte and including a pair of rearwardly spaced joints (56, 57) to facilitate a universal adjustability of said positioning calotte (52); and a bearing component (53) being connected to a rear end of said holder (55), said bearing component (53) extending transversely of longitudinal center plane and including bearing recesses (69) at opposite ends to enable positioning thereof on said joint elements (36).

2. A device according to claim 1, wherein said joint elements (36) include ball heads (36*a*).

3. A device according to claim 2, wherein said joint elements (36) comprise horizontal pins having the ball heads (36*a*) arranged thereon.

4. A device according to claim 2, wherein said bearing component (53) is releasably mounted on said ball heads (36*a*).

5. A device according to claim 4, wherein the bearing component (53) has transversely telescopable parts, and said bearing recesses (69) are formed by conical centering recesses in end faces of said bearing component, and said bearing component is seated coaxially on the ball heads (36*a*).

6. A device according to claim 5, wherein biasing means stresses said telescopable parts of the bearing component (53) against the joint elements (36).

7. A device according to claim 1, wherein at least one of said spaced joints (56, 57) is a ball joint.

8. A device according to claim 1, wherein carrying means for said holder (55) is arranged between the bearing component (53) and the positioning calotte (52), said carrying means being selectively connected and positioned in close fit with the bearing component (53) and positioning calotte (52) by a quick-action coupling (59) or plug-in socket (62).

9. A device according to claim 8, wherein said plug-in socket (62) comprises a plug-in recess (71) arranged on the bearing component and a plug-in pin (63) arranged on the holder (55), said pin being securable in the plug-in recess (71).

10. A device according to claim 9, wherein said plug-in pin is an upright support shaft (63) positionable in the upright, plug-in recess (71) which is selectively orientable in a forwardly and rearwardly open position through a horizontal movement, such that a section of the bearing component having the plug-in recess (71) is retained between a shoulder on the support shaft (63), said shoulder being formed by a transverse pin (72) and a nut (73) which is screwed onto a free end of the support shaft (63).

11. A device according to claim 10, wherein centering means are constituted by a transverse groove for the transverse pin (72) and a conical surface for a complementary conical surface (75) on the nut (73).

12. A device according to claim 10, wherein said spaced joints (56, 57) are arranged on the holder (55), and the support shaft (63) is rigidly connected with a joint ball (81) on the joint (56) associated therewith.

13. A device according to claim 1, wherein said positioning calotte (52) includes a support rod (58) of selectively angular and round cross-section extending horizontally rearwardly, and the bearing component (53) or the holder (55) has a socket comprising an aperture for receiving the support rod (58) and in which the support rod (58) is fixable in position.

14. A device according to claim 13, wherein the aperture is arranged in a joint ball (82) of a proximate joint (57) in the positioning calotte (52).

15. A device according to claim 14, wherein a common fixing member fixes said spaced joints (56, 57) in position, said fixing member being a fixing screw (83), the fixing member for the joints (56, 57) being operative at specified times, such that upon actuation of the fixing member only one joint is initially released or fixed and thereafter the other said joint is released or fixed.

16. A device according to claim 15, wherein the joint ball (82) possessing the aperture is slit, and the resultant clamping connection between the joint ball (82) and the support rod (58) is selectively released or fixed by the same fixing member (83) concurrently with the associated joint.

17. A device according to claim 1, wherein said positioning calotte (52) is adapted for the fabrication of full denture rows of teeth, said calotte having a convexly curved lower surface **(52*a*) and a holder component formed by a projecting carrying rod (58), said positioning calotte (52*a*) being formed of plastics or transparent material and including a plane upper surface (84)**.

* * * * *